United States Patent [19]
Landers et al.

[11] Patent Number: 5,953,115
[45] Date of Patent: Sep. 14, 1999

[54] METHOD AND APPARATUS FOR IMAGING SURFACE TOPOGRAPHY OF A WAFER

[75] Inventors: William Francis Landers, Wappingers Falls, N.Y.; Jyothi Singh, Houston, Tex.

[73] Assignee: International Business Machines Corporation, Armonk, N.Y.

[21] Appl. No.: 08/959,091

[22] Filed: Oct. 28, 1997

[51] Int. Cl.[6] .................................................. G01N 21/00
[52] U.S. Cl. .......................... 356/237; 356/135; 356/385
[58] Field of Search ..................... 356/237, 135, 356/385

[56] References Cited

U.S. PATENT DOCUMENTS

| | | | |
|---|---|---|---|
| 3,873,209 | 3/1975 | Schinke at al. | 356/135 |
| 4,905,293 | 2/1990 | Asai et al. | |
| 4,924,085 | 5/1990 | Kato et al. | |
| 5,125,740 | 6/1992 | Sato et al. | 356/135 |
| 5,280,334 | 1/1994 | Gisin et al. | 356/135 |
| 5,321,264 | 6/1994 | Kuwabara et al. | |

*Primary Examiner*—Frank G. Font
*Assistant Examiner*—Reginald A. Ratiff
*Attorney, Agent, or Firm*—Ratner & Prestia; Jay H. Anderson

[57] ABSTRACT

A method for imaging surface topography is based on Total Internal Reflection (TIR) and is particularly useful for imaging surface topography of wafers used in the manufacture of integrated circuits. This surface topography includes scratches, which are more localized, and dishing, which is a gentle dip over a larger area. In practice, a wafer is placed with the surface of interest in close contact with a prism or other internal reflection element (IRE). Light of suitable wavelength is incident at a suitable incident angle through the IRE of suitable refractive index in order to allow total internal reflectance at the surface of the IRE in close contact with the wafer surface. The reflected beam is then imaged to give a map of the location and dimensions, and some information on the depth, of the various surface features on the wafer.

18 Claims, 1 Drawing Sheet

METHOD AND APPARATUS FOR IMAGING SURFACE TOPOGRAPHY OF A WAFER

BACKGROUND OF THE INVENTION

1. Field of the Invention

The present invention relates to polished wafer surfaces for use in the manufacture of semiconductors, integrated circuits, and the like. More particularly, this invention relates to the detection of surface irregularities in such polished wafer surfaces.

2. Description of Related Art

During conventional semiconductor manufacturing, surface oxide layers of silicon wafers typically are polished using a chemical and mechanical polishing procedure known as chemical-mechanical polish (hereinafter CMP). The CMP procedure is tightly controlled to produce substantially flat polished wafer surfaces by periodically sampling polished wafers and examining surfaces for microscopic irregularities such as scratches, dishing, and the like. Conventional methods for examining wafer surfaces include methods based on light scattering. These sampling and examination methods are time consuming and inefficient. Consequently, a quantity of defective wafers may be produced before corrective adjustments can be made.

In addition to the surface topography of the silicon wafer, it is advantageous to evaluate the wafer surface for impurities contained in the surface. Kuwabara et al., U.S. Pat. No. 5,321,264, discloses a method for evaluating the surface of a silicon wafer in which an internal reflection element having a larger refractive index than silicon is brought directly into close contact with the surface of the silicon wafer. Light, from a light source having a wavelength range which can be absorbed by compounds on the wafer surface, enters the element at an incident angle which is larger that the critical angle. The light undergoes multiple reflections within the element with concomitant selected absorption by surface impurities. The chemical bond state of the wafer surface and the impurities are then spectrographically evaluated from the multiple-reflected light emanating from the end of the element.

A conventional method for electronically imaging human fingerprints uses a light beam which is incident on a glass/air interface at a critical angle or larger, to produce an uneven surface pattern of a fingerprint pressed on the glass/air interface. In this method, a detection apparatus uses a prism. The finger surface pattern which has macroscopic ridges and grooves is pressed against the base of the prism, and light from a light source is made incident on the oblique side at a critical angle or larger. The incident light is scattered by the ridges and is totally reflected by the glass/air interface in the grooves, and is then incident on a detector (e.g., an imaging element), to detect the macroscopic, uneven surface pattern. In practice, light may leak through unclean oblique surface areas caused by remaining fingerprints or moisture. This scattered light can lower the level of the signal and the contrast of the fingerprint pattern. To address such deficiencies, improvements on this method have been disclosed in U.S. Pat. No. 4,905,293 and No. 4,924,085, and in Japanese Patent Applications No. 58-158583 and No. 59-171112.

There is an industry need in the manufacture of semiconductors to continually monitor polished wafer surfaces after CMP in order to detect any microscopic irregularities and promptly make corrective adjustments to minimize defective wafers and waste.

SUMMARY OF THE INVENTION

This and other needs are met by the surface monitoring method of the present invention. The method detects and images irregularities in a flat, polished surface on an object. The object has an index of refraction $n^O$, the flat polished surface has an index of refraction $n^S$, and air has an index of refraction $n^{air}$. The irregularities are indentations into the flat polished surface. The method includes the following steps:

A. providing a transparent base having an optically flat surface, an incident surface, an exit surface, and an index of refraction $n^b$;

B. contacting the flat polished surface of the object to the optically flat surface of the transparent base to form an interface;

C. directing a beam of radiation, having a spectral band width with a central wavelength, through the incident surface of the transparent base onto the interface at an angle θ which is greater than a critical angle defined by the relationship of $n^b$ and $n^{air}$, to produce reflected radiation from the irregularities which passes through the exit surface of the transparent base; and D. detecting and converting the reflected radiation into a visible image of the irregularities.

BRIEF DESCRIPTION OF THE DRAWING

The invention can be more fully understood from the following detailed description in connection with the accompanying drawing described as follows.

DETAILED DESCRIPTION OF THE INVENTION

Figure 1:
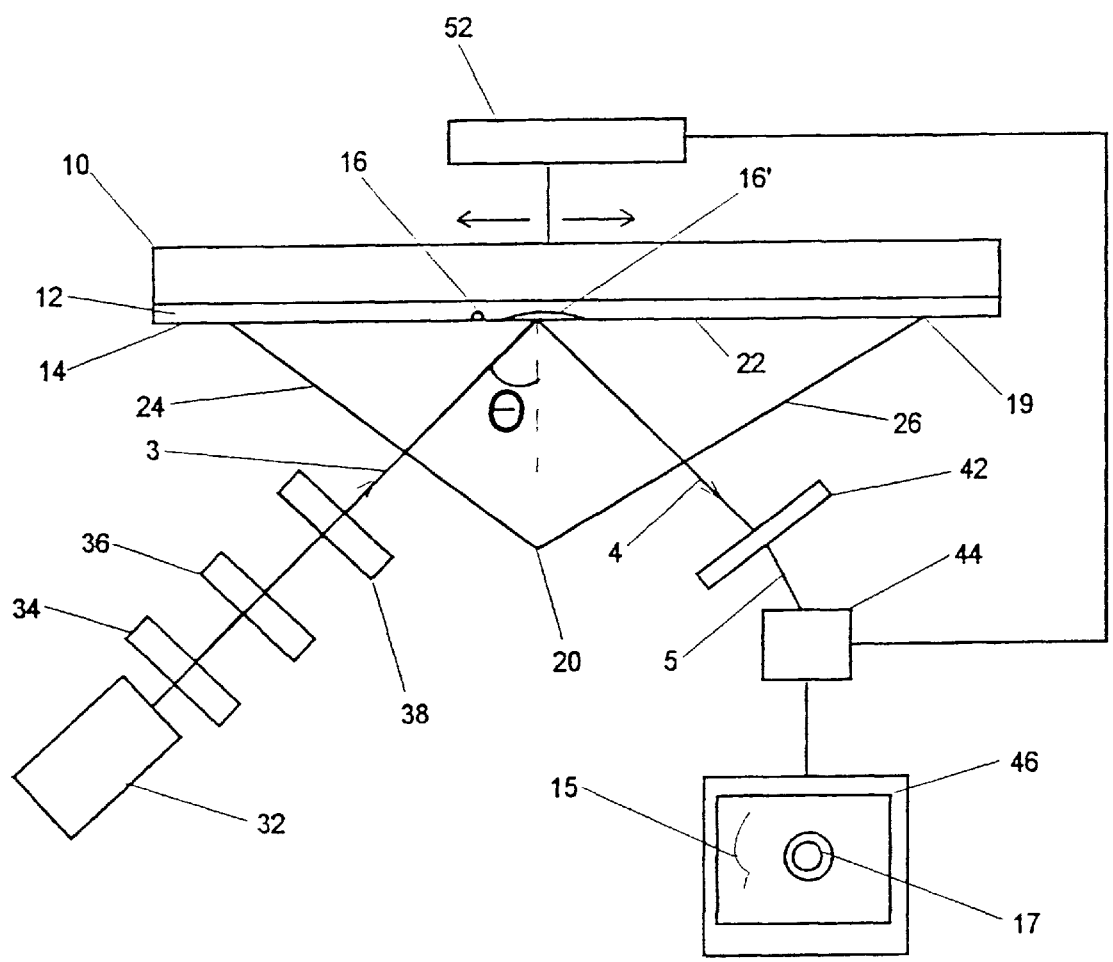
FIG. 1 illustrates details of the method of the present invention and the components used in that method.

The method of this invention for imaging surface topography is based on Total Internal Reflection (TIR) and is particularly useful for imaging surface topography of wafers used in the manufacture of integrated circuits. This surface topography includes scratches, which are more localized, dishing which is a gentle dip over a larger area, and bow. Scratches, dishing, and bow are typical process problems in CMP. Consequently, it is useful to monitor wafer surfaces during processing so as to rapidly detect problems, thus avoiding yield loss, reducing scrap and thereby lowering costs.

In the practice of the method according to the present invention, the wafer is placed with the surface of interest in close contact with a prism or other internal reflection element (IRE). Light of suitable wavelength is incident at a suitable incident angle through the IRE of suitable refractive index in order to allow total internal reflectance at the surface of the IRE in close contact with the wafer surface. The reflected beam is then imaged to get information about the surface topography of the wafer. Thus, this method gives a map of the locations and dimensions, and some information on the depth, of the various surface features on the wafer.

Information about dishing and scratches is obtained because surface relief is imaged with high contrast and good signal-to-noise ratio when conditions are adjusted so that total internal reflectance is attained in the regions of scratches or dishing (recessed structures) but not in the regions where the wafer surface is flat and makes good contact with the IRE surface. This is accomplished by altering the material of the IRE element and the angle of incidence of the incident light. Further, information about the depth of these surface features can be obtained by controlling the depth of penetration of the evanescent wave into the rarer medium at the TIR interface by varying the angle of incidence, the medium of incidence, and the wavelength of the incident light.

Referring to FIG. 1, the method of the present invention detects and images irregularities 16 and 16' in a flat, polished surface 14 on an object 10 such as a wafer used in the manufacture of integrated circuits and the like. The irregularities are indentations, such as scratches 16 or dishing 16', into the flat polished surface 14. As used herein, the term "dishing" is intended to mean a broad, shallow, concave void in the otherwise flat surface 14 of the object 10. As used herein, $n^O$ is the index of refraction of the object 10, $n^S$ is the index of refraction of the flat polished surface layer 12, and $n^{air}$ is the index of refraction of air which is present in the irregularities 16 and 16'.

The method of the present invention includes at least four steps. First, a transparent base 20, such as a prism, is provided which has an optically flat surface 22, an incident surface 24, and an exit surface 26. The transparent base 20 has an index of refraction $n^b$. The flat polished surface 14 of the object 10 is then contacted to the optically flat surface 22 of the transparent base 20 to form an interface 19 between the object 10 and the base 20. Any suitable device may be used to bring and maintain the flat polished surface 14 in intimate contact with the optically flat surface 22 during the imaging process.

A beam of radiation 3 having a spectral band width with a central wavelength is then directed through the incident surface 24 of the transparent base 20 onto the interface 19 at an angle θ which is greater than a critical angle defined by the relationship of $n^b$ and $n^{air}$, to produce reflected radiation 4 from the irregularities 16 and 16' which passes though the exit surface 26 of the transparent base 20. As used herein, the term "transparent base" is intended to mean that the base 20 is substantially transparent to the incident beam of radiation 3. The relationship which defines the critical angle is well known to be the $\sin^{-1}$ of the ratio of the indices of refraction for the two respective mediums forming the interface, i.e., $\sin^{-1}(n^{air}/n^b)$.

The reflected radiation 4 which passes through the exit surface 26 is then detected by an image detector 42 such as by a conventional CCD device. Then the detected signal 5 is converted in an electronic device 44 such as a computer, by conventional methods, to produce a visible image of the irregularities either on a monitor screen 46, or as a printed image (not illustrated in the figure), or both. (Image 15 corresponds to irregularity 16 and image 17 corresponds to irregularity 16'.) At the same time, the converted information may be stored for archival purposes or may be used to alter process parameters.

The object 10 may have any shape and may be composed of any solid material provided that it has at least one flat, polished surface 14. The method of the present invention is particularly useful for inspecting the polished surfaces of wafers used for manufacture of electronic components such as integrated circuits, semiconductor devices, and the like. Such wafers are typically composed of purified silicon or germanium and have a thin surface functional layer of oxide, nitride, metal, or the like. Typically, such functional layers are between about 0.1 and about 10 micrometers thick and have an index of refraction $n^S$ which is different from the index of refraction of the wafer, $n^O$. In contrast, native oxide layers which are present on semiconductor materials typically are between about 20 Å to about 100 Å thick. In other instances, when the object 10 is composed of an oxide such as silica, the compositions of the flat polished surface 14 and the object 10 are the same and, consequently, their indices of refraction are the same, i.e., $n^O = n^S$.

Although the method of the present invention is useful for inspecting polished surfaces of objects having only a native oxide surface or a surface which is the same as that of the object, this method is particularly useful for inspecting polished surfaces of functional layers, and most particularly for inspecting such functional surfaces which have been polished by a CMP method. Hereinafter, the method of the present invention will be described in reference to the object 10 being a silicon wafer for illustration purposes but the method is not intended to be limited by that description. Likewise, the surface layer 12 will be described hereinafter as a functional oxide layer for illustration purposes, unless otherwise indicated.

The transparent base 20 may have any shape provided that it has an optically flat surface 22, an incident surface 24, and an exit surface 26. Preferably, the transparent base 20 is a simple prism wherein one side forms the optically flat surface 22, and the other two sides form the incident surface 24 and the exit surface 26, respectively. The transparent base 20 may be composed of any solid material and typically has an index of refraction, $n^b$, which is substantially greater than $n^S$. When the object 10 is a wafer, the transparent base preferably is composed of silicon, germanium, sapphire, magnesium fluoride, or the like. Hereinafter, the method of this invention will be described in reference to the transparent base 20 being a prism which is composed of silicon, germanium, sapphire, or magnesium fluoride, for illustration purposes, but the method is not intended to be limited by that description.

The incident beam of radiation 3 originates as light from a radiation source 32 which consists of the radiation source itself along with the associated optics to collimate the emitted radiation into a radiation beam. The radiation source 32 may be a laser or a broad band radiation source which may emit in the visible spectral region, the infrared region, or both regions. The radiation beam then passes through a wavelength selector 34 (if desired) to isolate radiation with a desired bandwidth and central wavelength. Suitable wavelength selectors 34 include band pass filters, monochromators, and the like. The wavelength selected radiation is then polarized in a polarizer 36 preferably to be parallel to the plane of incidence. The angle of incidence θ of the polarized beam of radiation 3 onto the interface 19, between the flat polished surface 14 of the wafer 10 and the optically flat surface 22 of the prism, is controlled using an optical member 38. The light source 32 may be a broad band light source which emits in the visible region, in the infrared region, or in both spectral regions. Suitable broad band light sources include tungsten lamps, carbon arcs, glow bars, and the like. When a narrow band beam of radiation 3 is desired, the light source preferably is a laser, such as an infrared laser, which also obviates the need for the wavelength selector 34.

The angle of incidence θ of beam of radiation 3 onto the interface 19, the radiation central wavelength, and the index of refraction of the prism 20 are selected so that at least the index of refraction of the prism $n^b$ is greater than the index of refraction of air $n^{air}$ which fills the voids formed by scratches 16 and dishing 16' in the surface layer 12 of the wafer 10. In particular, to effectively image surface relief, the values of $n^b$ and incident angle θ are chosen so that θ is greater than the critical angle for the air/prism interface, but smaller than the critical angle for the wafer surface/prism interface. In fact, it is desirable to arrange θ to be just less than the critical angle for the wafer surface/prism interface because, for parallel polarized incident radiation under these conditions, the intensity of the parallel polarized reflected radiation is close to zero, while that for the air/prism interface is almost total, i.e., the image contrast is high and good surface relief maps of the scratches or dishing may be obtained.

Thus, for optimum imaging of irregularities 16 and 16', the incident angle θ is greater than a critical angle defined by the relationship of $n^b$ and $n^{air}$, and is also less than a second critical angle defined by the relationship of $n^b$ and $n^S$. The resulting totally internally reflected beam 4 is then imaged using a suitable visible or infrared image detector 42, such as a CCD device. The signal from the detector is then processed by suitable electronics 44 to yield an image of surface relief in the local region.

Monitoring the entire wafer surface involves translation device 52 which moves the wafer 10 across the optically flat surface 22 of the prism 20. The translation device 52 either provides a signal to the electronic device 44 to indicate the position of the wafer 10 on the prism 20 or, alternatively, the translation device 52 is controlled by the electronic device 44 to provide a desired position. The localized images can be blended over the different regions of the wafer to yield the total wafer map of surface relief which is displayed on a monitor screen 46, printed on a suitable printer, or both. Typically, the electronic device 44 is a computer which reduces the input signal from the image detector 42 to a digital record which can be further processed with other related information to produce the wafer map viewed on the monitor.

During normal use of the method according to the present invention, numerous wafers are translated across the optically flat surface 22 of the prism 20 and the prism surface itself can be expected to receive some scratches. To eliminate possible confusion between prism scratches and any scratches on the wafer surface 14, an optical flat which is known to be free of scratches is first examined under the conditions of intended use and a record is made of the map of the optically flat surface 22, including any scratches in optically flat surface 22. This record is then used to subtract any noted prism scratches from maps of wafer surfaces subsequently inspected.

Penetration depth of the evanescent wave in the rarer medium following total internal reflection is given by the relationship:

$$d = \frac{\lambda}{2\pi n^b [\sin^2\theta - (n^{rare}/n^b)^2]^{1/2}}$$

where d is the distance for the electric field amplitude to decrease to 1/e of its value at the surface. Therefore, by increasing the wavelength λ, decreasing the angle of incidence θ, and decreasing the refractive index $n^b$ of the prism 20 (but still keeping it higher than that of the wafer surface layer 12), it is possible to gradually increase the penetration depth. Thus, for a given prism, either the angle θ may be varied to vary the penetration depth of the radiation into the interface 19, or the central wavelength may be varied to vary the penetration depth of the radiation into the interface 19. Alternatively, both the central wavelength as well as the angle of incidence may be varied. Such variations produce maps of the surface relief at different penetration depths which provide an indication of the depths of different regions within the scratch 16 or dishing 16'.

By way of example, assume that it is desired to image an oxide wafer having an index of refraction of 1.46. If a sapphire prism is used, the critical angle for the sapphire-quartz interface is about 56 degrees, while that for the sapphire-air interface is only 35 degrees. For light of wavelength 1550 nm (from a diode laser), at an angle of incidence of 45 degrees, the penetration depth in air is about 333 nm. However, for 308 nm light (from an eximer laser) at an incident angle of 50 degrees, the penetration depth in air is only about 54 nm. The former dimension is more typical of dishing; the latter dimension is more indicative of some scratches. Under these conditions, there will be no total internal reflection at the sapphire-quartz interface because the incident angle is less than the critical angle for the sapphire-quartz interface. Thus only the scratches, dishing or other irregularities in the wafer surface are imaged, while the smooth regions on the (quartz) wafer surface making good contact with the sapphire base are not imaged.

In another embodiment of the present invention, the chemical nature of the wafer surface may be examined along with the detection of any irregularities. In this embodiment, spectral bands of the incident radiation 3 which penetrates the interface 19 may be absorbed by chemical species within the surface layer 12 so that resulting reflected radiation 4 is deficient in the absorbed bands. Such absorbed spectral bands or wavelengths are characteristic of specific chemical bond types within the chemical species.

To accomplish this analysis, a portion of the reflected radiation 4 is analyzed spectroscopically to determine the composition of the flat polished surface 14. To optimize this analysis and provide for maximum surface absorption, the incident angle θ is selected to be greater than a critical angle defined by the relationship of $n^b$ and $n^S$, and the critical angle defined by the relationship of $n^b$ and $n^{air}$. Typically, the reflected radiation may be analyzed spectroscopically by selecting a broad spectral band width of the incident beam of radiation 3 to encompass the infrared spectral region. The reflected broad band radiation is analyzed spectroscopically by conventional dispersive methods or by FTIR spectroscopy. Alternatively, the incident radiation may be chosen to have a narrow band width which is tuned across the desired spectral region to provide a spectral signature of the surface of the object.

Those skilled in the art having the benefit of the teachings of the present invention, as set forth above, can effect numerous modifications to the invention. These modifications are to be construed as being encompassed within the scope of the present invention as set forth in the appended claims.

What is claimed is:

1. A method for detecting and imaging irregularities in a flat, polished surface on an object, wherein the object has an index of refraction $n^O$, the flat polished surface has an index of refraction $n^S$, and air has an index of refraction $n^{air}$ and wherein the irregularities are indentations into the flat polished surface, the method comprising:

A. providing a transparent base having an optically flat surface, an incident surface, an exit surface, and an index of refraction $n^b$;

B. contacting the flat polished surface of the object to the optically flat surface of the transparent base to form an interface comprising an air/transparent base interface section at the irregularities;

C. directing a beam of radiation, having a spectral band width with a central wavelength, through the incident surface of the transparent base onto the interface at an angle θ which is greater than a critical angle defined by the relationship of $n^b$ and $n^{air}$, to produce totally internally reflected radiation at the air/transparent base interface section at the irregularities which passes through the exit surface of the transparent base; and D. detecting and converting the reflected radiation into a visible image of the irregularities.

2. The method of claim 1 wherein the object is a wafer comprising one of silicon and germanium.

3. The method of claim 2 wherein the flat polished surface is one of an oxide, nitride, and metal surface layer.

4. The method of claim 3 wherein the flat polished surface was polished by a chemical-mechanical polishing method.

5. The method of claim 1 wherein compositions of the flat polished surface and the object are the same and wherein $n^O = n^S$.

6. The method of claim 1 wherein the angle $\theta$ is less than a second critical angle defined by the relationship of $n^b$ and $n^S$.

7. The method of claim 1 wherein the transparent base is selected from the group consisting of silicon, germanium, sapphire, and magnesium fluoride.

8. The method of claim 1 wherein the beam of radiation is a laser beam.

9. The method of claim 1 wherein the beam of radiation is infrared radiation.

10. The method of claim 1 wherein the flat polished surface is translated across the optically flat surface.

11. The method of claim 1 wherein the transparent base is a prism.

12. The method of claim 1 wherein the reflected radiation is detected and converted into the visible image electronically and wherein the visible image is displayed as an image on at least one of a monitor and a printer.

13. The method of claim 1 wherein the irregularities are at least one of scratches and concave voids.

14. The method of claim 1 wherein the angle $\theta$ is varied whereby penetration depth of the radiation into the interface is varied.

15. The method of claim 1 wherein the central wavelength is varied whereby penetration depth of the radiation into the interface is varied.

16. A method for detecting and imaging irregularities in a flat, polished surface on an object, wherein the object has an index of refraction $n^O$, the flat polished surface has an index of refraction $n^S$, and air has an index of refraction $n^{air}$ and wherein the irregularities are indentations into the flat polished surface, the method comprising:

A. providing a transparent base having an optically flat surface, an incident surface, an exit surface, and an index of refraction $n^b$;

B. contacting the flat polished surface of the object to the optically flat surface of the transparent base to form an interface;

C. directing a beam of radiation, having a spectral band width with a central wavelength, through the incident surface of the transparent base onto the interface at an angle $\theta$ which is greater than a critical angle defined by the relationship of $n^b$ and $n^{air}$ and which is greater than a second critical angle defined by the relationship of $n^b$ and $n^S$, to produce reflected radiation from the irregularities which passes through the exit surface of the transparent base; and D. detecting and converting the reflected radiation into a visible image of the irregularities wherein a portion of the reflected radiation is analyzed spectroscopically to determine the composition of the flat polished surface.

17. The method of claim 16 wherein the band width of the beam of radiation encompasses at least one of the visible spectral region and the infrared spectral region, and wherein the reflected radiation is analyzed spectroscopically with a spectrograph.

18. The method of claim 16 wherein the band width of the beam of radiation is narrowed to within a few wavelengths of the central wavelength and the central wavelength is varied through at least one of the visible spectral region and the infrared spectral region, whereby the reflected radiation is analyzed spectroscopically.

* * * * *